United States Patent
Fischer

(10) Patent No.: US 8,246,632 B2
(45) Date of Patent: Aug. 21, 2012

(54) DEVICE FOR ENDOSCOPIC REMOVAL OF STONES OR CONCREMENTS FROM A BILE AND PANCREATIC DUCT OR FOREIGN BODIES AND POLYPS SUBSEQUENT TO POLYPECTOMY IN THE UPPER OR LOWER GASTROINTESTINAL TRACT

(75) Inventor: Gerald Fischer, Hoechstadt/Aisch (DE)

(73) Assignee: Medwork Medical Products and Services GmbH, Hoechstadt/Aisch (DE)

( * ) Notice: Subject to any disclaimer, the term of this patent is extended or adjusted under 35 U.S.C. 154(b) by 167 days.

(21) Appl. No.: 12/790,459

(22) Filed: May 28, 2010

(65) Prior Publication Data

US 2011/0004056 A1 Jan. 6, 2011

Related U.S. Application Data

(60) Provisional application No. 61/222,149, filed on Jul. 1, 2009.

(51) Int. Cl.
*A61B 17/221* (2006.01)

(52) U.S. Cl. ..................................................... 606/127

(58) Field of Classification Search .................. 600/104; 606/106, 110, 113–115, 127, 200
See application file for complete search history.

(56) References Cited

U.S. PATENT DOCUMENTS

| 6,059,796 | A | * | 5/2000 | Bilitz et al. | 606/127 |
| 6,077,274 | A | | 6/2000 | Ouchi et al. | |
| 2005/0154378 | A1 | * | 7/2005 | Teague et al. | 606/2.5 |
| 2007/0255289 | A1 | * | 11/2007 | Nakao | 606/113 |

FOREIGN PATENT DOCUMENTS

| DE | 3615694 Y | 11/1987 |
| DE | 9014246 Y | 1/1991 |
| DE | 19841480 Y | 12/2002 |
| EP | 1442716 A | 3/2008 |
| EP | 1528893 Y | 7/2009 |
| JP | 2000126194 Y | 5/2000 |

* cited by examiner

*Primary Examiner* — Ryan Severson
*Assistant Examiner* — Ashley Cronin
(74) *Attorney, Agent, or Firm* — Lucas & Mercanti, LLP

(57) ABSTRACT

A device (1) for endoscopic removal of stones or concrements from a bile and pancreatic duct or foreign bodies and polyps subsequent to polypectomy in the upper or lower gastrointestinal tract comprises a cable (9) guided in a tube (2) and further comprises, on its proximal end, an actuation element (3) for an axial displacement of the cable (9) within the tube (2). The cable (9) receives, on its distal end, a collecting basket (16) formed by at least four elastic basket wires (17), said basket wires (17) being bundled at one end on the cable (9) and at another end on a guide element (18). The basket wires (17) bear against the end of the tube (2) such that an axial displacement of the cable (9) leads to a loop-like contraction or expansion of the collecting basket (16) and to a twisting of the collecting basket (16) about its longitudinal axis. The tube (2) is configured as a double-lumen tube, the cable (9) being arranged in a first lumen (8) and a guide wire (5) being arranged in a second lumen (19), and a distal end of the guide wire (5) extending axially beyond the tube (2) is not guided relative to the collecting basket (16).

9 Claims, 2 Drawing Sheets

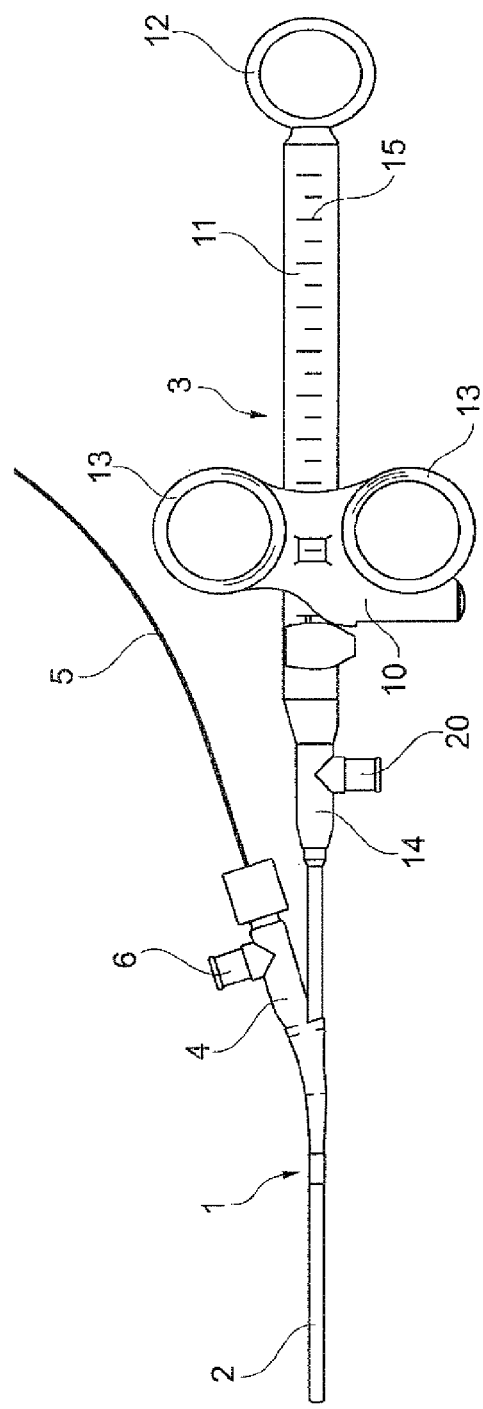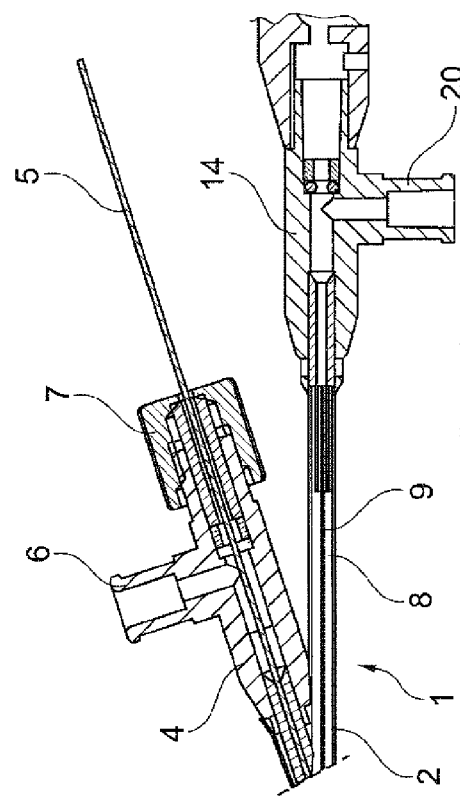

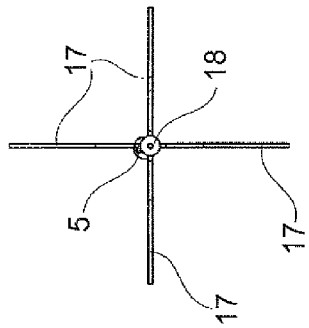
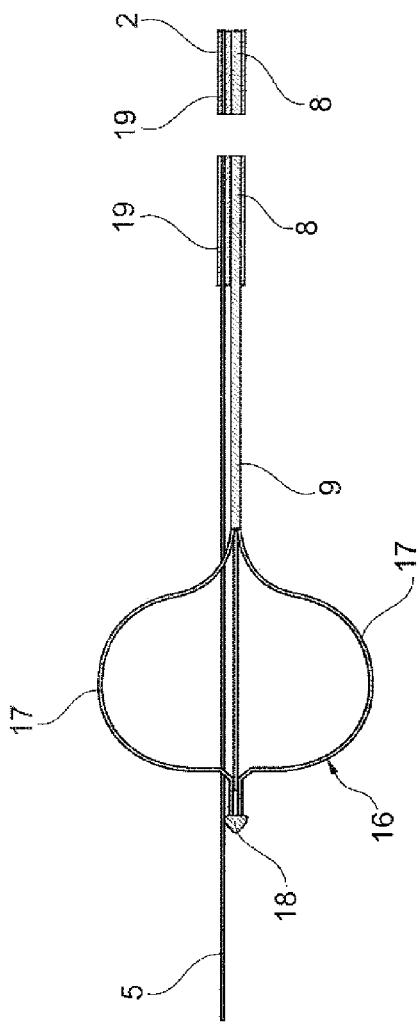
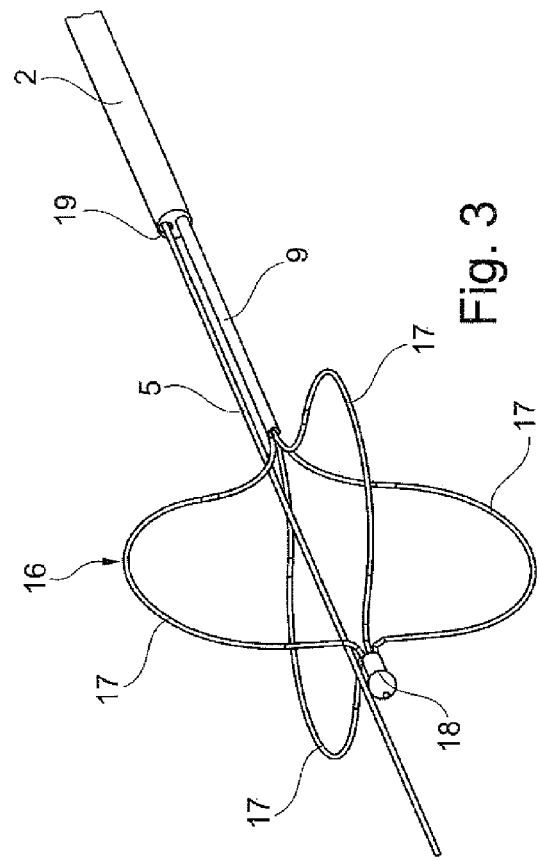

DEVICE FOR ENDOSCOPIC REMOVAL OF STONES OR CONCREMENTS FROM A BILE AND PANCREATIC DUCT OR FOREIGN BODIES AND POLYPS SUBSEQUENT TO POLYPECTOMY IN THE UPPER OR LOWER GASTROINTESTINAL TRACT

CROSS REFERENCE TO RELATED APPLICATIONS

This application claims the benefit of U.S. Provisional Application 61/150,473, 61/222,149 filed Jul. 1, 2009 which is incorporated by reference herein

FIELD OF THE INVENTION

The invention concerns a device for endoscopic removal of stones or concrements from a bile and pancreatic duct or foreign bodies and polyps subsequent to polypectomy in the upper or lower gastrointestinal tract, said device comprising a cable guided in a tube comprising on a proximal end, an actuation element for an axial displacement of the cable within the tube and said cable comprising on a distal end, a collecting basket formed by at least four elastic basket wires, said basket wires being bundled at one end on the cable and at another end on a guide element, those basket wires which bear against the end of the tube leading, upon an axial displacement of the cable, to a loop-like contraction or expansion of the collecting basket and to a twisting of the collecting basket about a longitudinal axis of the collecting basket. The designation of the ends of the device as distal and proximal is to be understood as relative to an operator of the device.

In most cases, for removing a gallstone out of a bile and pancreatic duct, the gallstone is at first made to come free from the papilla by means of a further endoscopic device. The endoscopic device used for this purpose, which is also called a sphincterotome, serves for probing and opening the papilla by means of a high frequency current. Following this and using the generic device, the gallstone disengaged out of the papilla, is captured by the rotating and simultaneously contracting collecting basket in that the gallstone is clamped between the basket wires and thus fixed in the collecting basket. The removal of foreign bodies or polyps from the upper or lower gastrointestinal tract is realized in a similar manner. In case of removal of polyps, these are at first separated from the mucous membrane by means of a polypectomy loop and removed from the digestive tract subsequently by means of the collecting basket. During this procedure, the reliable capturing of the polyp is likewise considerably aided by the fact that the collecting basket twists and simultaneously contracts continually, so that the polyp, clamped between the basket wires, can be reliably removed.

A generic device for endoscopic removal of stones or concrements from a bile and pancreatic duct or foreign bodies and polyps subsequent to polypectomy in the upper or lower gastrointestinal tract is known from the document DE 198 41 480 C2. This known device comprises a single-lumen tube with the cable guided in the lumen being connected at its proximal end to the bundled basket wires of the collecting basket. The basket wires and the end of the tube cooperating with these during contraction of the collecting basket are designed such that the axial movement of the collecting basket relative to the tube causes a rotation of the collecting basket.

The document EP 1 442 716 B1 discloses an endoscopic device whose collecting basket, which can be contracted through the cable or expanded by reason of its own internal stress, comprises basket wires intended to execute only an axial movement. Therefore, no turning movement of the collecting basket is provided. The device comprises a double-lumen tube, firstly for guiding the cable and secondly for receiving a guide wire. The guide element comprises an opening for a guide wire at the proximal end of the collecting basket. The guide wire projecting out of the lumen of the tube is inserted through this opening with circumvention of the collecting basket. By this, it is intended to prevent the guide wire from obstructing the stone from entering into the interior of the collecting basket.

SUMMARY OF THE INVENTION

It is therefore the object of the invention to provide a device comprising a rotary collecting basket that can be introduced into narrow body openings.

The invention achieves the above object by the fact that the tube is configured as a double-lumen tube, the cable being arranged in a first lumen and a guide wire being arranged in a second lumen, and a distal end of the guide wire extending axially beyond the tube is not guided relative to the collecting basket. In preparation of an extraction of stones, the distal end of the guide wire extending beyond the tube and having a very flexible configuration, can be pushed right into the required position and then guides, via the corresponding lumen, the entire device which is pushed with its distal end into the region of the stone. Because the guide wire projects only from the lumen of the tube and is guided neither relative to this nor to the cable or the collecting basket, no obstruction of the rotary movement and the outward movement of the collecting basket takes place. The collecting basket can therefore be pushed by means of the cable into its opened position for receiving the stone.

In comparison, the prior art device does not comprise any guide wire for introducing the device into the very narrow bile and pancreatic duct. Difficulties are encountered as a rule with prior art devices in placing them distally in the narrow bile and pancreatic duct and removing gallstones with the help of the rotating collecting basket. If, according to the further cited prior art solution, the guide wire is guided at the distal end of the collecting basket, this arrangement of the guide wire is not suitable for a configuration of the device with a collecting basket that can be twisted by reason of a longitudinal movement of the cable.

In contrast to the above, in the device of the invention, the tip of the guide wire and the proximal end of the collecting basket are freely movable relative to each other. For capturing the gallstone, it is very important that the guide wire be able to avoid the collecting basket and thus also the gallstone, so that the capturing of the gallstone is not impeded. In addition, the collecting basket must be able to execute a rotational movement without being hindered in doing this by the guide wire.

According to a further development of the invention, the collecting basket has a spherical outer contour in its expanded state. This shape is particularly suitable for the extraction of stones with no obstruction whatever of the movements of the collecting basket being caused by the guide wire which extends in the region of the collecting basket.

Moreover, the guide wire can penetrate right through the spatial stretch of the expanded collecting basket. Due to the geometry of the collecting basket and the manner in which the guide wire extends relative to the basket wires, no hindrance of the contracting and simultaneously rotating collecting basket occurs. Because, as already set forth, the guide wire possesses no guidance at the proximal end, the reception of the stone into the collecting basket is not obstructed either. According to the invention, the collecting basket advantageously executes a rotation through approximately 130° which, due to the reciprocal movement of the cable, takes place automatically.

Moreover, the guide element in which the basket wires are bundled together advantageously has a cartridge-shaped configuration. This guide element is dimensioned such that it can be fully retracted into the tube. Alternatively, however, it is also possible to configure the guide element with a mushroom shape, so that atraumatic characteristics of the distal end can be assured, i.e. soft parts are not injured.

According to another proposition of the invention, it is further possible to arrange between the proximal end of the tube and the actuation element, a first sluice branching off at an acute angle from the tube, the longitudinal channel of this sluice serving to receive the guide wire being connected with the second lumen. The guide wire extends out of this first sluice and can thus be moved manually.

According to still another proposition of the invention, the first sluice comprises a nipple for introducing a liquid into the lumen which receives the guide wire. A further sluice is arranged on the first lumen which receives the cable and a liquid can likewise be supplied through this connecting nipple. The liquid supplied through the second lumen can particularly be a contrast medium.

An advantageous handling of the endoscopic device is enabled by the fact that the actuation element comprises a guide shaft which is connected to the tube and comprises a longitudinal slit, the actuation element further comprising a slide which is connected to the cable and guided in this longitudinal slit. The guide shaft may be provided with a thumb ring whereas the slide is configured in one piece with two finger rings.

BRIEF DESCRIPTION OF THE DRAWING

Further features of the invention will result from the following description and the appended drawing, in which one example of embodiment of the invention is illustrated in a simple manner. The figures show:

FIG. 1, a proximal end of an endoscopic device of the invention,

FIG. 2, a detail out of the proximal end of the device of FIG. 1, as a longitudinal section.

FIG. 3, a portion of the distal end of the device and a representation of an opened collecting basket, FIG. 4, a section through the distal end of the device with the opened collecting basket, and FIG. 5, a top view of the opened collecting basket of FIGS. 3 and 4

DETAILED DESCRIPTION OF THE DRAWING

In FIGS. 1 and 2, a device for an endoscopic removal of stones and concrements is identified at 1 and comprises a tube 2 and an actuation element 3. A first sluice 4 through which a guide wire 5 is inserted into the tube 2 is arranged between the actuation element 3 and the tube 2. This first sluice 4 further comprises a nipple 6 for supplying liquids and is sealed by a cap 7 surrounding the guide wire. As can be seen further in FIGS. 1 and 2, the first sluice 4 extends at an acute angle to the tube 2. A cable 9 is arranged within a first lumen 8 in the tube 2. The actuation element 3 comprises a slide 10 connected to the cable, said slide 10 being guided in a longitudinal slit of a guide shaft 11 which likewise forms a part of the actuation element 3. This guide shaft 11 in its turn is fixedly connected to the tube, so that through a movement of the slide relative to the guide shaft, the cable 9 can be moved to and fro within the tube 2. For executing this movement, the guide shaft 11 is provided with a thumb ring 12, while the slide comprises two finger rings 13.

Between the tube 2 and the actuation element 3 is further arranged a second sluice 14 through which liquids can likewise be supplied which then penetrate into the first lumen 8. The guide shaft 11 of the actuation element 3 further comprises a scale 15 for enabling a simpler handling of the device.

FIGS. 3 to 5 further disclose the configuration of the distal end of the device. In FIGS. 3 and 4 is identified at 16 a collecting basket whose basket wires 17 are shown in a state in which the collecting basket 16 is in its opened position. The basket wires 17 are bundled at their ends, on one side at the end of the cable and on the other side in a cartridge-shaped guide element 18. The cable 9 extends in the first lumen 8 of the tube 2. The tube 2 further comprises a second lumen 19 in which the guide wire 5 extends. This guide wire 5, as can be seen in FIGS. 3 to 5, extends through the spatial stretch of the collecting basket. The guide wire 5 guided according to the invention in the second lumen possesses no guidance whatever at its distal end, so that it obstructs neither the movement of the collecting basket 16 nor the reception of stones into the collecting basket.

In the run-up to an endoscopic removal of stones or foreign bodies, the collecting basket 16 is at first moved into its closed position in which it is fully contained in the tube 2. The guide wire 5 projecting far out of the second lumen 19 is then inserted into the body opening concerned and moved under endoscopic or radiological observation into the region of the stone or foreign body. Subsequent to this, the entire endoscopic device 1 is made to follow on the guide wire 5 and the collecting basket 16 is opened through the actuation element 3. The opening of the collecting basket is caused by its own internal stress, the collecting basket being released through a movement of the slide 10 relative to the guide shaft 11. In this opened position, the collecting basket 16 captures the stone in question and executes a rotary movement while capturing the stone and during its own closing movement. Following this, the stone can be extracted by means of the device 1. Because the guide wire 5 is configured to move freely in the second lumen 19, it can remain in the body of the patient temporarily for carrying out further treatment.

LIST OF REFERENCE NUMERALS

1 Device for endoscopic removal of stones and concrements
2 Tube
3 Actuation element
4 First sluice
5 Guide wire
6 Nipple
7 Cap
8 First lumen
9 Cable
10 Slide
11 Guide shaft
12 Thumb ring
13 Finger ring
14 Second sluice
15 Scale
16 Collecting basket
17 Basket wires
18 Guide element
19 Second lumen

The invention claimed is:

1. A device for endoscopic removal of stones or concrements from a bile and pancreatic duct or foreign bodies and polyps subsequent to polypectomy in the upper or lower gastrointestinal tract, said device comprising:
   a cable guided in a tube;
      the tube comprising, on a proximal end, an actuation element for an axial displacement of the cable within the tube;
      said cable comprising, on a distal end, a collecting basket formed by at least four elastic basket wires;
         said basket wires being bundled at one end on the cable and at another end on a guide element, those basket wires which bear against the end of the tube leading, upon an axial displacement of the cable, to a loop-like contraction or expansion of the collecting basket and to a rotation of the collecting basket about a longitudinal axis of the collecting basket,
   wherein
   the tube is configured as a double-lumen tube, the cable being arranged in a first lumen and a guide wire being arranged in a second lumen, and the first lumen extends next to the second lumen within the tube;
   a distal end of the guide wire extending axially beyond the tube is not guided relative to the collecting basket; and
   the collecting basket executes the rotation through approximately 130°.

2. The device of claim 1 wherein in an expanded state, the collecting basket has a spherical outer contour.

3. The device of claim 1 wherein in an expanded state the guide wire penetrates through a spatial stretch of the expanded collecting basket.

4. The device of claim 1 wherein the guide element has a cartridge-shaped configuration.

5. The device of claim 1 wherein a first sluice branching off at an acute angle from the tube is arranged between the proximal end of the tube and the actuation element, a longitudinal channel of this sluice serves to receive the guide wire and is connected with the second lumen.

6. The device of claim 5 wherein a nipple for introducing a liquid into the lumen which receives the guide wire branches off from the first sluice.

7. The device of claim 5 wherein a second sluice is arranged between the actuation element and the first sluice, said second sluice receives the cable and comprises a connecting nipple which is connected with the first lumen.

8. The device of claim 1 wherein the actuation element comprises a guide shaft which is connected to the tube and comprises a longitudinal slit, the actuation element further comprising a slide which is connected to the cable and guided in said longitudinal slit.

9. The device of claim 8, wherein the guide shaft comprises a thumb ring and the slide is configured in one piece with two finger rings.

* * * * *